United States Patent
Stradella et al.

(10) Patent No.: US 7,828,172 B2
(45) Date of Patent: Nov. 9, 2010

(54) DOSE INDICATOR FOR FLUID PRODUCT DISPENSING DEVICE

(75) Inventors: Fabio Stradella, Camogli (IT); Giuseppe Stradella, Camogli (IT)

(73) Assignee: Valois S.A.S., Le Neubourg (FR)

( * ) Notice: Subject to any disclaimer, the term of this patent is extended or adjusted under 35 U.S.C. 154(b) by 1140 days.

(21) Appl. No.: 10/564,748

(22) PCT Filed: Jul. 13, 2004

(86) PCT No.: PCT/FR2004/001846

§ 371 (c)(1), (2), (4) Date: Jun. 21, 2006

(87) PCT Pub. No.: WO2005/017463

PCT Pub. Date: Feb. 24, 2005

(65) Prior Publication Data

US 2007/0029341 A1 Feb. 8, 2007

(30) Foreign Application Priority Data

Jul. 18, 2003 (FR) .................................. 03/08834

(51) Int. Cl.
*B67D 7/22* (2010.01)
(52) U.S. Cl. .................. 222/36; 128/205.23; 215/230
(58) Field of Classification Search .................. 222/30, 222/32, 36, 22, 39–49, 162, 205.23, 200.18, 222/200.24; 128/200.14, 200.17, 200.23, 128/200.12, 200.15; 116/306, 309; 215/230
See application file for complete search history.

(56) References Cited

U.S. PATENT DOCUMENTS

| 5,349,945 | A | | 9/1994 | Wass et al. |
|---|---|---|---|---|
| 5,421,482 | A | * | 6/1995 | Garby et al. .................. 222/36 |
| 5,482,030 | A | * | 1/1996 | Klein ..................... 128/200.23 |
| 5,611,444 | A | * | 3/1997 | Garby et al. ................. 215/230 |
| 5,718,355 | A | * | 2/1998 | Garby et al. .................. 222/36 |
| 5,779,651 | A | * | 7/1998 | Buschmann et al. ........ 600/587 |
| 6,679,251 | B1 | * | 1/2004 | Gallem et al. .......... 128/200.23 |
| 6,769,601 | B2 | * | 8/2004 | Haikarainen et al. ...... 235/87 R |
| 6,997,349 | B2 | * | 2/2006 | Blacker et al. ................. 222/23 |
| 7,191,918 | B2 | * | 3/2007 | Ouyang et al. ................ 222/36 |
| 7,195,134 | B2 | * | 3/2007 | Ouyang et al. ................ 222/36 |
| 7,407,066 | B2 | * | 8/2008 | Ouyang et al. ................ 222/36 |
| 2007/0210102 | A1 | * | 9/2007 | Stradella et al. ............... 222/36 |
| 2007/0235027 | A1 | * | 10/2007 | Schuckmann .......... 128/200.17 |
| 2008/0210230 | A1 | * | 9/2008 | Lintern et al. .......... 128/200.23 |

FOREIGN PATENT DOCUMENTS

| GB | 1336014 | * | 6/1970 |
| WO | WO 00/09187 A1 | | 2/2000 |
| WO | WO 01/37909 A1 | | 5/2001 |
| WO | WO 0137909 A1 | * | 5/2001 |

* cited by examiner

*Primary Examiner*—Lien T Ngo
(74) *Attorney, Agent, or Firm*—Sughrue Mion, PLLC

(57) ABSTRACT

The invention relates to a dose indicator (A) which is intended for a fluid product dispensing device (B). The inventive indicator consists of at least one rotary counting means (10) which can move in rotation and which comprises indicator means (15), said indicator means indicating the number of doses that have been distributed or that remain to be distributed. Moreover, said at least one counting means is actuated by an actuation member (35) which is in turn actuated by a transmission element (34) that is designed to co-operate with the dispensing device each time the latter is actuated. The dose indicator comprises amplification means which are designed to amplify the movement of the transmission element (34) with each actuation, such that the movement of the actuation member (35) is greater than the movement of the transmission element (34).

51 Claims, 4 Drawing Sheets

DOSE INDICATOR FOR FLUID PRODUCT DISPENSING DEVICE

BACKGROUND OF THE INVENTION (1) Field of the Invention

The present invention relates to a dose indicator and to a device for dispensing fluid products which comprises said indicator.

(2) Description of Related Art

In the area of fluid product dispensing devices intended to dispense several doses, in particular in the area of sprays, numerous systems have been developed intended to indicate the number of dispensed doses or the number of doses remaining to be dispensed.

Most of these systems have numerous drawbacks. For example they are generally designed with several toothed wheels forming cogs whose number is dependent upon the quantity of doses to be counted. Therefore these counters or indicators may become highly complex, cumbersome and hence costly to manufacture and assemble. Also, the indication is generally given in figures which are often difficult to read by the user, especially when the dispensing devices are intended to dispense a large number of doses, e.g. up to 200 doses. Similarly, all current dose counter or indication systems cannot be used by persons with sight problems, by blind persons in particular. Another major disadvantage lies in the fact that existing counters generally require an assembly procedure for the dispensing device which is modified through the presence of the counter, and therefore differs from usual assembly procedure. This increases the complexity of the device and consequently entails a higher cost.

In addition, one very important safety requirement is to prevent any risk of under-counting i.e. failure to count full or partial dispensing of the product. To avoid this risk, the actuation of the counter must be made during the motion of the dispensing member, in particular of the dispensing valve, which occurs before product expelling is initiated. The initial motion distance is generally very short, typically in the order of 1 to 1.5 mm and the various size tolerances of the device reduce this distance to a few tenths of millimetres. Such a short actuation distance makes actuation of the counter difficult and may involve the use of complex mechanisms to guarantee functional counting.

BRIEF SUMMARY OF THE INVENTION

The purpose of the present invention is to provide a dose indicator for a fluid product dispensing device which does not reproduce the above-mentioned disadvantages.

In particular, the purpose of the present invention is to provide a dose indicator which is simple and low cost to manufacture and assemble, and which may in particular be applied to all existing fluid product dispensing devices without involving a modification in assembly procedure.

Another object of the invention is to provide a dose indicator of small size, irrespective of the number of doses contained in the dispensing device.

A further object of the invention is to provide a dose indicator which forms a complete, separate unit and which in particular comprises the means for actuating the indicator.

A still further object of the invention is to provide a dose indicator which is easy to read by the user and which may be used by persons having sight problems, by blind persons in particular.

Yet another object of the invention is to provide a dose indicator which avoids any risk of under-counting (the non-taking into account of a dispensed dose). More particularly, the purpose of the present invention is to provide a dose indicator which counts right at the start of the actuation distance of the dispensing device with which it is associated, even if this distance is very short.

The subject of the present invention is therefore a dose indicator for fluid product dispensing device, comprising at least one rotary counting means movable in rotation, said at least one rotary counting means comprising indication means indicating the number of doses dispensed or remaining to be dispensed, said at least one rotary counting means being actuated by an actuating member itself actuated by a transmission element adapted to cooperate with one part of said dispensing device whenever it is actuated, said dose indicator comprising amplification means adapted to amplify the movement of said transmission element on each actuation so that the movement of said actuating member is greater than the movement of said transmission element.

Advantageously, said at least one rotary counting means comprises a rotary counting wheel with cogging, said cogging cooperating with actuating means adapted to cause said rotary disk to rotate, said actuating means comprising a flexible lug comprising a first flexible lug part and a second flexible lug part more rigid than the first lug part, the first lug part bearing an actuating tooth adapted to cooperate with the cogging of said rotary counting wheel on each actuation of the device, and the second part of the lug bearing the transmission element adapted to cooperate with said fluid product dispensing device whenever it is actuated, the second lug part being attached firstly to said first lug part and secondly to said transmission element, resulting in amplified movement of said actuating tooth with respect to the movement of said transmission element.

Advantageously, said flexible lug is joined to a ring surrounding said cogging, said flexible lug coming to cooperate with said cogging whenever a dose is dispensed.

Advantageously, said ring comprises anti-reverse means preventing said rotary disk from rotating in the opposite direction to the direction induced by said flexible lug.

Advantageously, said ring comprises an abutment that is adapted to cooperate with a locking element joined to said flexible lug to limit rotation of said rotary counting wheel.

Advantageously the second, more rigid, lug part is adapted to deflect on and after the time when the locking element is locked by the abutment means of the ring.

Advantageously, the rotation of the rotary counting wheel occurs at the start of the actuation distance of the fluid product dispensing device, the flexion of the second, more rigid lug part allowing said actuation distance of the fluid product dispensing device to be completed up to its end despite the locking of the locking element by the abutment means.

Advantageously, said transmission element is a shoulder joined to a flexible lug and cooperating with one part of the fluid product dispensing device which is mobile during actuation.

Advantageously, the indicator comprises a translatable member which can be moved in translation, the indication means cooperating with a display opening provided in said translatable member, said at least one rotary counting means comprising a rotary counting wheel comprising a hollow profile cooperating with a projection of said translatable member, the shape of said hollow profile being such that at least some rotations of said rotary counting wheel give rise to translation of said translatable member, modifying the position of said translatable member with respect to said counting wheel.

Advantageously, said rotary counting wheel and said translatable member are arranged in a lid comprising a display window cooperating with the display opening of the translatable member.

Advantageously, the rotary counting wheel, the translatable member, the actuation means and the lid form a unit which may be assembled in a fluid product dispensing device.

Advantageously, said indication means follow said hollow profile at least in part.

Advantageously, the shape of said hollow profile is irregular so that dose indication is progressive.

Advantageously, said hollow profile is at least in part of spiral shape.

Advantageously, said indication means are numbers and/or symbols.

Advantageously, said amplification means transform a translation movement a of the transmission element into a rotary movement of the actuation member, the translation projection of said rotary movement being $\alpha.a$, where $\alpha>1$.

Advantageously, said second flexible lug part comprises an elastically deformable structure.

Advantageously, said second flexible lug part comprises two branches forming an ovoid structure having two opposite apexes formed firstly by the transmission element and secondly by the junction with the first lug part, said ovoid structure capable of being stretched through the movement of said transmission element and elastically returning to its rest position when the transmission element is not urged anymore.

A further subject of the invention is a fluid product dispensing device comprising a product reservoir and a dispensing member, such as a pump or valve, mounted on said reservoir, and a dose indicator such as defined above.

Advantageously, the dose indicator is actuated by part of the dispensing device which is moved on actuation of the device, and which cooperates with a transmission element of said indicator.

BRIEF DESCRIPTION OF THE DRAWINGS

Other characteristics and advantages of the present invention will become more apparent in the following detailed description of a particular embodiment thereof, made with reference to the appended drawings given as non-restrictive examples and in which.

DETAILED DESCRIPTION OF THE PREFERRED EMBODIMENTS OF THE INVENTION

The dose indicator A of the present invention applies to all types of fluid product dispensing devices. However, it applies more particularly to spray devices, and advantageously to aerosol devices comprising a dose measuring valve mounted on a recipient containing a product and a propellant gas.

Figure 1:
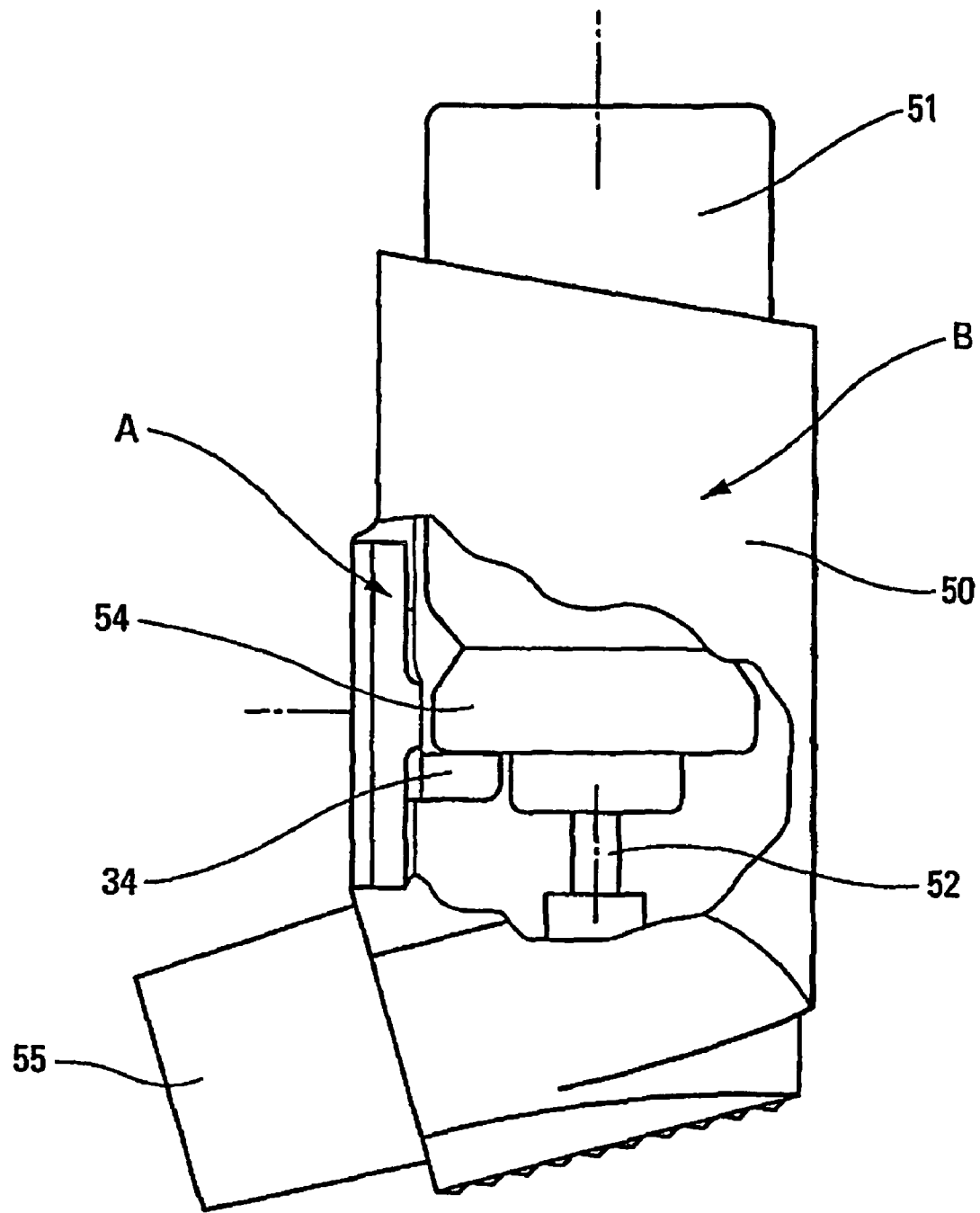
FIG. 1 is a partially cut-out side view diagram of a fluid product dispensing device comprising a dose indicator according to an advantageous embodiment of the present invention.
Figure 2:
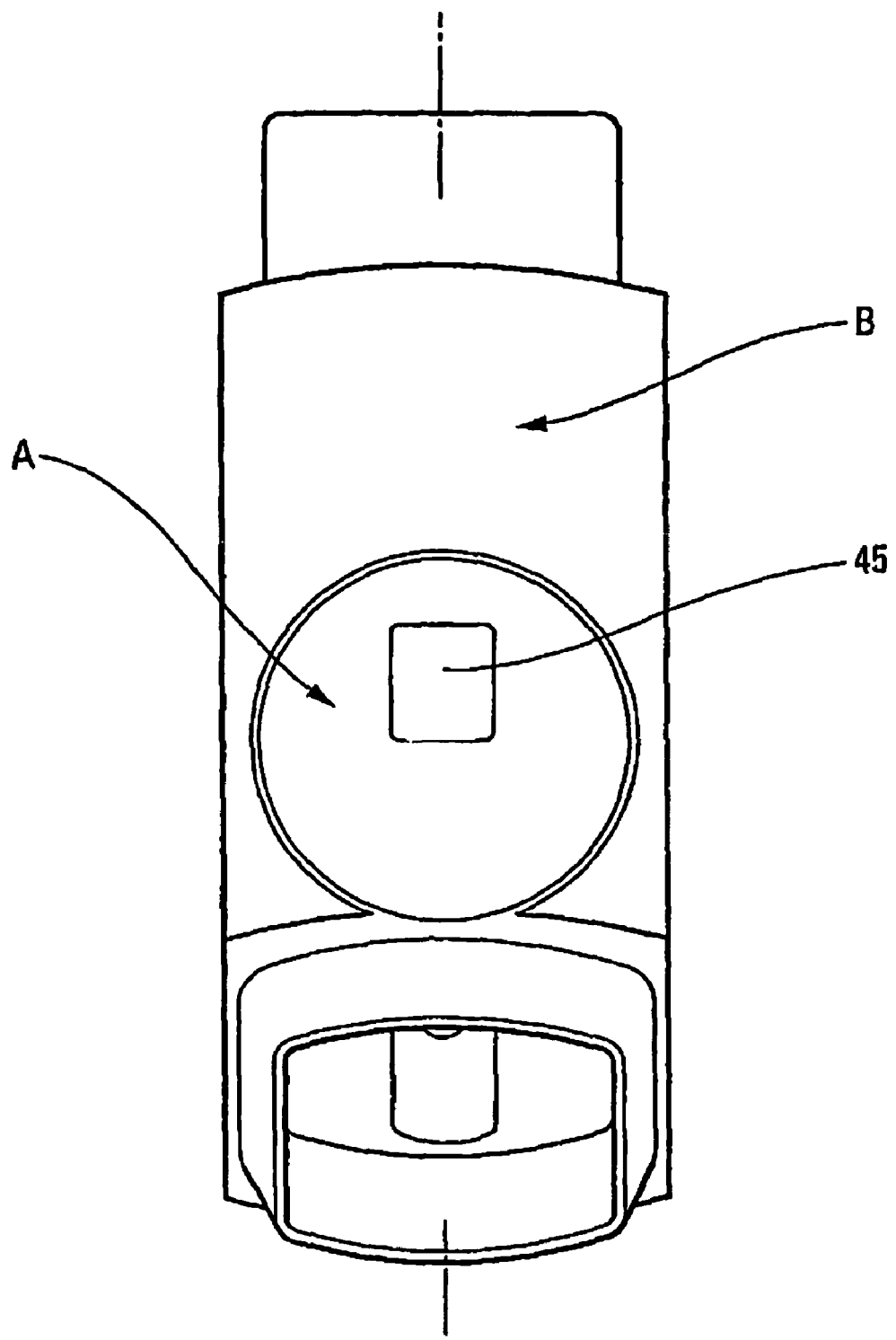
FIG. 2 is a front view, similar to the view in FIG. 1.
Figure 3:
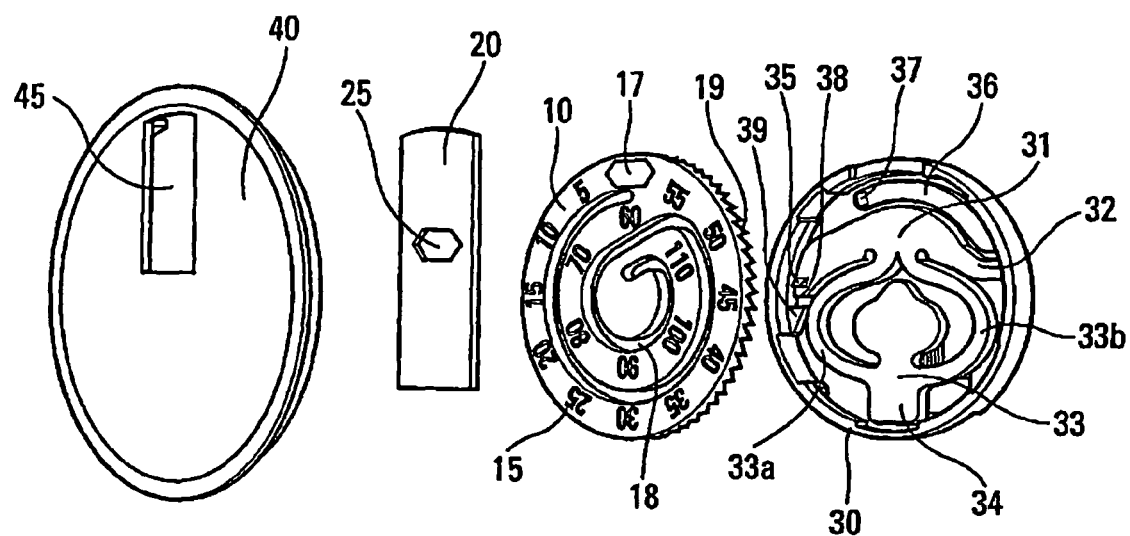
FIG. 3 is an exploded view of a dose indicator according to an advantageous embodiment of the invention.
Figure 4:
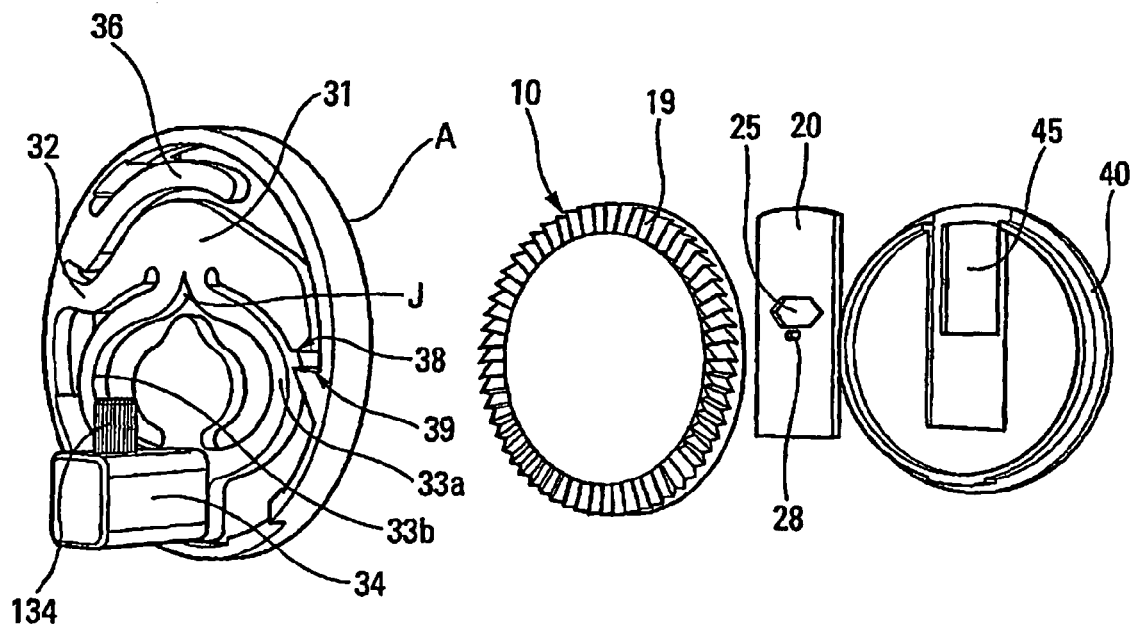
FIG. 4 is a similar view to FIG. 3, viewed from another angle.

FIGS. 1 and 2 schematically show a dispensing device B to which the dose indicator A of the present invention is particularly adapted. This device comprises a body 50 and a reservoir 51 on which a dose-measuring valve 52 is assembled. Actuation of device B is obtained by axial movement of reservoir 51 within body 50, this movement causing compression of the valve 52 which causes the expelling of a dose of product through a mouth opening 55. Evidently, the present invention also applies to other types of dispensing devices, in particular to spray devices of nasal type or devices comprising a pump instead of the valve.

FIGS. 3 to 7 show a dose indicator A which may particularly be used with a fluid product dispensing device B described above. This dose indicator comprises at least one rotary counting means which, in the illustrated example, is formed by a rotary counting wheel 10, preferably made in the form of a rotary disc adapted to move in rotation about a rotation axis substantially perpendicular to said disc 10. This rotary disc 10 is preferably thin and provided with a hollow profile 18 which may advantageously be formed by a rib or groove. Disc 10 also advantageously comprises a set of teeth or cogging 19 preferably arranged on its periphery, said cogging 19 being adapted to cooperate with the actuation means which are adapted to cause said disc 10 to rotate, and which will be described in more detail below. The counting disc or wheel 10 also comprises indication means 15 which may be numbers and/or symbols and intended to indicate the number of doses dispensed or remaining to be dispensed. These indication means 15 advantageously follow said hollow profile 18 at least in part.

Indicator A shown in the figures may also advantageously comprise a translatable member 20 adapted to move in translation. This translatable member 20 comprises a projection 28, or any other equivalent means, which cooperates with said hollow profile 18 of the rotary disc 10. This translatable member 20 is preferably made in the form of a thin plate, and comprises a display opening 25 intended to cooperate with the indication means 15 of the rotary disc 10.

Depending upon the shape of the hollow profile 18, a rotation of the counting wheel 10 can cause translation of the translatable member 20. Advantageously, profile 18 is made so that the indication is progressive and non-regular. For example, the indicator in FIGS. 3 and 4 may count around 120 doses, the last 50 being displayed in intervals of 5 in the display opening 25 of the translatable member 20, whereas the first doses are indicated in intervals of 10. In this example, the hollow profile 18 is firstly of spiral shape in the centre of disc 10 so that each rotation of said disc 10 causes translation of said translatable member 20. When only 50 doses remain to be dispensed, the profile 18 becomes cylindrical so that the following rotations of disc 10 no longer cause movement of the translatable member 20. The indication means 15 are then displayed in the display opening 25 when the device is actuated. After the last dose, a specific symbol 17 may indicate that there are no doses remaining to be dispensed. Other progressions also may be contemplated.

Advantageously, the counting wheel 10 and the translatable member 20 are arranged in a lid 40 which is preferably also of thin structure and comprises a display window 45 cooperating with the display opening 25 of the translatable member 20 to enable the user to visualize the indication means 15 of the counting wheel 10.

Actuation of indicator A, and in particular rotation of the rotary counting wheel 10 may advantageously be produced by actuation means integrated in said indicator A. These actuation means may advantageously comprise a driving element 31 in the form of a flexible lug joined to a ring 30 which surrounds said cogging 19 of the rotary disc 10. This flexible lug 31 is adapted to cooperate with said cogging 19 whenever a dose is dispensed, preferably by means of an actuation member 35 such as a tooth. Advantageously, anti-reverse means 36, 37 are provided to prevent said rotary disc 10 from rotating in the opposite direction to the direction imparted to it by the flexible lug 31 at the time of actuation. These anti-reverse means may comprise a flexible lug 36 bearing an anti-reverse tooth 37 cooperating with cogging 19.

The actuation means also comprise a transmission element 34 adapted to cooperate with the fluid product dispensing device B whenever it is actuated, said transmission element 34 also cooperating with said flexible lug 31 to cause said rotary disc 10 to rotate. In particular, as can be seen FIG. 1, said transmission element 34 is a shoulder joined to the flexible lug 31 and which cooperates with a part 54 of the fluid product dispensing device B which is mobile during actuation. In the example illustrated, this is the attachment ring 54 of the dose-measuring valve 52 on reservoir 51. Evidently, and more generally, any part which moves during actuation of device B is adapted to cooperate with shoulder 34 to actuate the dose indicator A. Advantageously, the transmission element 34 may comprise an adjustable pin 134 to compensate for manufacturing tolerances when assembling the dispensing device, and may have variable actuation distances to pre-determine the actuation distance of indicator A.

With reference to FIGS. 3 to 7, the flexible lug 31 may be provided with two flexible parts 32 and 33 of different flexibility, the first part 32 being more flexible than the second part 33. The second lug part 33 bears said shoulder 34, and when the spray device B is actuated the attachment ring 54 of the reservoir firstly causes the more flexible part 32 of arm 31 to deflect parallel to the rotary disc 10, which causes rotation of said disc 10 by means of the actuation tooth 35 which cooperates with cogging 19. The flexible lug 31 advantageously comprises a locking element 38 adapted to cooperate with a projecting abutment 39 joined to ring 30. The radial distance between the locking element 38 and abutment 39 advantageously corresponds to a tooth of cogging 19. Therefore, during actuation, shoulder 34 is moved (downwards in the figures) by the dispensing device B, and the more flexible part of arm 32 deflects (also downwards in the figures) until the locking element 38 contacts the abutment 39 as can be seen FIG. 6. This leads to rotation over the equivalent of a tooth of the counting wheel 10. The more flexible part of arm 32 is then locked, and continuation of the actuation distance of dispensing device B is possible through flexion of the least flexible part of arm 33 as can be seen FIG. 7. In this way actuation of the dose indicator is allowed over the first part of said actuation distance. This eliminates any risk of not counting a dispensed dose (either in full or in part) in the event of partial actuation of the dispensing device B, while allowing the actuation distance to be completed after counting. The abutment 39 and anti-reverse means 36, 37 ensure that each dose is only counted once.

Figure 5:
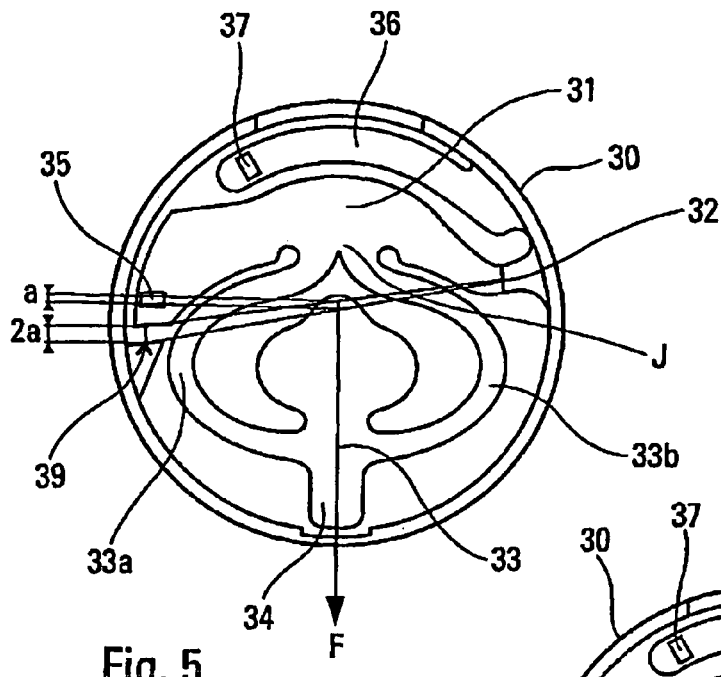
FIG. 5 is a schematic view of the actuation means of the indicator shown FIGS. 3 and 4, in rest position.
Figure 6:
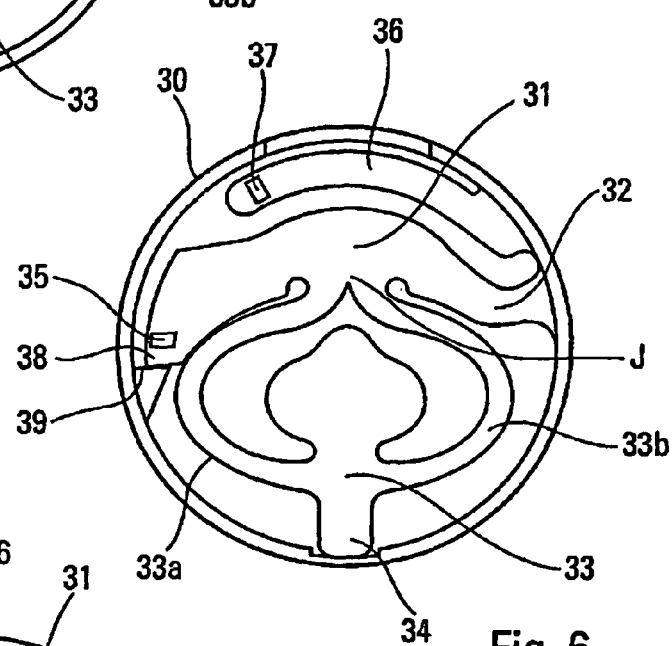
FIG. 6 is a similar view to FIG. 5 at the start of actuation.
Figure 7:
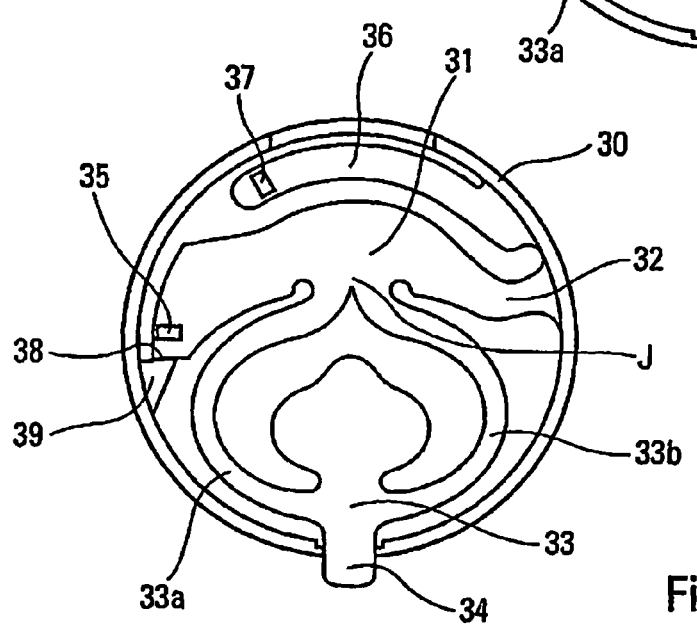
FIG. 7 is a similar view to FIGS. 5 and 6 at the end of actuation.

According to the invention, amplification means are provided adapted to amplify the movement of the transmission element 34 right at the start of the actuation distance so that the movement of the actuating member (tooth) 35 is greater than the movement of said transmission element 34. In the illustrated example, the second lug part 33 advantageously comprises two branches 33a and 33b. These branches are preferably convex and attached firstly to the first lug part 32 and secondly to the transmission element 34. As can be seen FIGS. 3 to 7, these branches 33a and 33b may form an ovoid structure with two opposite apexes, one formed by said junction J and the other formed by said transmission element 34. Movement of the transmission element 34 therefore causes stretching of this ovoid structure which pulls on the first lug part 32. FIG. 5 shows the amplification of the movement. The transmission element 34 is moved downwards in FIG. 5 at the start of the actuation distance in the direction of arrow F. The transmission element 34, and hence the second lug part 33, are moved in translation whereas the first lug part 32 is moved in rotation. The fact that junction J is offset with respect to the axis of rotation of the first lug part 32 causes amplification of the movement of tooth 35 positioned on the other side of junction J with respect to this axis of rotation. A translation projection of the movement of this tooth is schematically shown FIG. 5 and compared with the translation movement "a" of transmission element 34. In this example, in which the junction is approximately in the centre of the first lug part 32, it is found that the amplification factor is around 2. Evidently, by modifying the position of junction J it is possible to modify the amplification factor $\alpha$, bearing in mind that $\alpha$ will always be greater than 1. Advantageously, the second lug part 33 may be guided during its movement by appropriate means (not shown) provided in body 50 of the device for example. Advantageously, branches 33a and 33b return elastically to their rest position after actuation.

Evidently, the elastic structure with two convex branches could be replaced by any single-branch or multi-branch elastic structure of any shape. The only essential requirement is that this structure should be attached to the first lug part 32 and is elastically deformable so that firstly it causes rotary movement of the first lug part at the start of the actuation distance, and secondly it enables continued motion over the actuation distance up to its end.

The number of teeth on cogging 19 and the shape of the hollow profile 18 of the counting wheel 10 impart the characteristics of the dose indicator, and in particular the number of doses which this indicator can count. The maximum number of doses and the display mode may vary as desired by modifying the profile structure 18, the indication means or the number of teeth on cogging 19. With the present invention it is therefore possible to produce dose indicators that are adapted to count any number of doses without modifying the geometry or size of said indicator. As already specified above, the dimensional structure of the present indicator is particularly small, in particular it is of narrow thickness and this indicator A may therefore be very easily integrated into existing fluid product dispensing devices B as can be seen FIGS. 1 and 2.

The dose indicator of the present invention makes it possible to visualize in simple, low cost and progressive manner the number of doses dispensed or remaining to be dispensed in the device. The indicator structure is very thin irrespective of the number of doses it is to indicate, and it does not comprise any projecting part entailing modification of the device to which it is applied. As can be seen FIG. 1, the dose indicator A of the present invention can be applied very easily to all existing devices without the need to modify the same. The presence of indicator A does not modify the assembly process either of device B. The indicator may for example be positioned in device B through an opening provided for this purpose on the front part of body 50 of the device. A further advantage of the present indicator is that the actuation means of the indicator are integrated therein so that the indicator forms an independent, separate unit which may be pre-assembled and easily integrated into any fluid product dispensing device. The inventive dose indicator especially guarantees actuation of said indicator right at the start of the actuation distance, in particular over its initial part before dose expelling is initiated. Even when this initial distance is short, the amplification means of the present invention ensure reliable counting.

Evidently, the present invention has been described with reference to a particular embodiment thereof, illustrated in the drawings, but it is no way limited to this particular embodiment. On the contrary, persons skilled in the art will be able to make any modification thereto without departing from the scope of the present invention such as defined in the appended claims.

The invention claimed is:

1. Dose indicator (A) for fluid product dispensing device (B) comprising at least one rotary counting means (10) which can be moved in rotation, said at least one counting means comprising indication means (15) indicating the number of doses dispensed or remaining to be dispensed, said at least one counting means being actuated by an actuating member (35) itself actuated by a transmission element (34) adapted to cooperate with a moving part (54) of said dispensing device on each actuation thereof, wherein said dose indicator comprises amplification means adapted to amplify the movement of said transmission element (34) on each actuation, so that the movement of said actuating member (35) is greater than the movement of said transmission element (34).

2. Indicator as in claim 1, wherein said at least one rotary counting means comprises a rotary counting wheel (10) comprising cogging (19), said cogging (19) cooperating with actuating means (31,34,35) adapted to cause said rotary wheel (10) to rotate, said actuating means comprising a flexible lug (31) comprising a first flexible lug part (32) and a second flexible lug part (33) more rigid than the first lug part (32), the first lug part (32) bearing an actuating tooth (35) adapted to cooperate with cogging (19) of said rotary counting wheel (10) on each actuation of the device, the second lug part (33) bearing the transmission element (34) adapted to cooperate with said fluid product dispensing device (B) whenever it is actuated, the second lug part (33) being attached firstly to said first lug part (32) and secondly to said transmission element (34) resulting in an amplified movement of said actuating tooth (35) with respect to the movement of said transmission element (34).

3. Indicator as in claim 2, wherein said flexible lug (31) is joined to a ring (30) surrounding said cogging (19), said flexible lug (31) coming to cooperate with said cogging (19) whenever a dose is dispensed.

4. Indicator as in claim 3, wherein said ring (30) comprises anti-reverse means (36, 37) preventing said rotary disc (10) from rotating in the opposite direction to the direction induced by said flexible lug (31).

5. Indicator as in claim 3, wherein said ring (30) comprises an abutment (39) adapted to cooperate with a locking element (38) joined to said flexible lug (31) to limit the rotation of said rotary counting wheel (10).

6. Indicator as in claim 5, wherein the second, more rigid lug part (33) is adapted so that it deflects on and after the time the locking element (38) is locked by the abutment means (39) of the ring (30).

7. Indicator as in claim 2, wherein the rotation of the rotary counting wheel (10) occurs at the start of the actuation distance of the fluid product dispensing device (B), the flexion of the second, more rigid lug part (33) enabling said actuation distance of the fluid product dispensing device (B) to be completed up to its end despite locking of the locking element (38) by the abutment means (39).

8. Indicator as in claim 1, wherein said transmission element (34) is a shoulder joined to a flexible lug (31) and cooperating with the moving part (54) of the fluid product dispensing device (B) which is mobile during actuation.

9. Indicator as in claim 1, wherein the indicator (A) comprises a translatable member (20) which can be moved in translation, the indication means (15) cooperating with a display opening (25) provided in said translatable member (20), said rotary counting wheel (10) comprising a hollow profile (18) cooperating with a projection (28) of said translatable member (20), the shape of said hollow profile (18) being such that at least some rotations of said at least one counting means comprising a rotary counting wheel (10) give rise to translation of said translatable member (20), modifying the position of said translatable member (20) with respect to said counting wheel (10).

10. Indicator as in claim 9, wherein said rotary counting wheel (10) and said translatable member (20) are arranged in a lid (40) comprising a display window (45) cooperating with the display opening (25) of the translatable member (20).

11. Indicator as in claim 10, wherein the rotary counting wheel (10), the translatable member (20), the actuating means (31, 34, 35) and the lid (40) form a unit which can be assembled in a fluid product dispensing device (B).

12. Indicator as in claim 9, wherein said indication means (15) follow said hollow profile (18) at least in part.

13. Indicator as in claim 9, wherein the shape of said hollow profile (18) is irregular so that dose indication is progressive.

14. Indicator as in claim 9, wherein said hollow profile (18) is at least partly of spiral shape.

15. Indicator as in claim 1, wherein said indication means (15) are numbers and/or symbols.

16. Indicator as in claim 1, wherein said amplification means transform a translation movement, a, of the transmission element (34) into a rotary movement of the actuating member (35), the translation projection of said rotary movement being $\alpha.a$, where $\alpha>1$.

17. Indicator as in claim 2, wherein said second flexible lug part (33) comprises an elastically deformable structure.

18. Indicator as in claim 17, wherein said second flexible lug part (33) comprises two branches (33a, 33b) forming an ovoid structure having two opposite apexes formed firstly by the transmission element (34) and secondly by the junction (J) with the first lug part (32), said ovoid structure able to be stretched by movement of said transmission element (34) and returning elastically to its rest position the transmission element is not urged anymore.

19. Fluid product dispensing device (B) comprising a product reservoir (51) and a dispensing member (52) such as a pump or valve mounted on said reservoir (51), characterized in that it comprises a dose indicator (A) as in claim 1.

20. Device as in claim 19, wherein the dose indicator (A) is actuated by the moving part (54) of the dispensing device (B) which is moved during actuation of device (B) and which cooperates with a transmission element (34) of said indicator (A).

21. Dose indicator for fluid product dispensing device comprising at least one rotary means which can be moved in rotation, said at least one rotary means being actuated by actuating means connected to a transmission element adapted to cooperate with a moving part of said dispensing device on each actuation thereof, wherein said dose indicator comprises amplification means adapted to amplify the movement of said transmission element on each actuation, so that the movement of said actuating means is greater than the movement of said transmission element.

22. Indicator as in claim 21, wherein said actuating means comprises a first flexible part and a second flexible part more rigid than the first flexible part, said first flexible part cooperating with said rotary means on each actuation of the device, the second flexible part bearing the transmission element adapted to cooperate with said fluid product dispensing device when actuated.

23. Indicator as in claim 22, wherein said at least one rotary means comprises a rotary wheel comprising cogging, said cogging cooperating with actuating means adapted to cause said rotary wheel to rotate.

24. Indicator as in claim 23, wherein said actuating means comprise a flexible lug comprising a first flexible lug part and a second flexible lug part more rigid than the first lug part, the first lug part bearing an actuating tooth adapted to cooperate with cogging of said rotary wheel on each actuation of the device, the second lug part bearing the transmission element adapted to cooperate with said fluid product dispensing device when actuated, the second lug part being attached firstly to said first lug part and secondly to said transmission element resulting in an amplified movement of said actuating tooth with respect to the movement of said transmission element.

25. Indicator as in claim 24, wherein said flexible lug is joined to a ring surrounding said cogging, said flexible lug coming to cooperate with said cogging whenever a dose is dispensed.

26. Indicator as in claim 25, wherein said ring comprises anti-reverse means preventing said rotary wheel from rotating in the opposite direction to the direction induced by said flexible lug.

27. Indicator as in claim 25, wherein said ring comprises an abutment adapted to cooperate with a locking element joined to said flexible lug to limit the rotation of said rotary wheel.

28. Indicator as in claim 27, wherein the second, more rigid lug part is adapted to deflect on and after the time the locking element is locked by the abutment means of the ring.

29. Indicator as in claim 22, wherein the rotation of the rotary means occurs at the start of the actuation distance of the fluid product dispensing device, the flexion of the second, more rigid part enabling said actuation distance of the fluid product dispensing device to be completed.

30. Indicator as in claim 21, wherein said transmission element comprises a shoulder joined to a flexible lug and cooperating with the moving part of the fluid product dispensing device which is mobile during actuation.

31. Indicator as in claim 21, wherein said rotary means is arranged in a lid comprising a display window.

32. Indicator as in claim 31, wherein the rotary means, the actuating means and the lid form a unit which can be assembled in a fluid product dispensing device.

33. Indicator as in claim 21, wherein said amplification means transform a translation movement, a, of the transmission element into a rotary movement of the actuating means, the translation projection of said rotary movement being $\alpha.a$, where $\alpha>1$.

34. Indicator as in claim 22, wherein said second flexible part comprises an elastically deformable structure.

35. Indicator as in claim 34, wherein said second flexible part comprises two branches forming an ovoid structure having two opposite apexes formed firstly by the transmission element and secondly by the junction with the first flexible part, said ovoid structure able to be stretched by movement of said transmission element and returning elastically to a rest position when the transmission element is not urged anymore.

36. Fluid product dispensing device comprising a product reservoir and a dispensing member such as a pump or valve mounted on said reservoir, comprising a dose indicator as in claim 21.

37. Device as in claim 36, wherein the dose indicator is actuated by the moving part of the dispensing device which is moved during actuation of device and which cooperates with a transmission element of said indicator.

38. A dose indicator for fluid product dispensing device, the dose indicator comprising:
a rotary member rotatable about an axis; and
a disk member comprising a transmission element attached to a spring and positioned to engage the dispensing device and an actuation element attached to the spring at a location separate from the transmission element;
wherein movement of the transmission element moves the actuation element to incrementally rotate the rotary member; and
wherein the spring is shaped so that a given displacement of the transmission element causes a greater displacement of the actuation element.

39. The indicator as in claim 38, wherein the spring comprises a first flexible part and a second flexible part more rigid than the first flexible part, the first flexible part cooperating with said rotary member on each actuation of the device, the second flexible part bearing the transmission element.

40. Indicator as in claim 38, wherein the spring transforms a translation movement of the transmission element into a rotary movement of the actuation element.

41. A dose indicator for a fluid product dispensing device comprising:
a rotary counting wheel comprising markings indicating the number of doses dispensed or remaining to be dispensed;
an actuating member that is displaceable and rotates the counting wheel when displaced;
a transmission element that engages a moving part of the dispensing device on each actuation and is displaced transversely with respect to the markings on the counting wheel; and
a cantilever spring that amplifies the movement of the transmission element during each actuation, so that the displacement of the actuating member is greater than the displacement of the transmission element.

42. The dose indicator according to claim 41, wherein the transmission element is attached to a middle portion of the cantilever spring and the actuating member is attached to a distal end of the cantilever spring.

43. The dose indicator according to claim 41 further comprising:
a second spring disposed between the cantilever spring and the transmission element;
wherein the cantilever spring and the second spring are configured such that the cantilever spring is displaced before the second spring.

44. The dose indicator according to claim 1, wherein the transmission element is displaced in a translational direction.

45. The dose indicator according to claim 1, wherein a portion of the transmission element that cooperates with the moving part of the dispensing device is displaced a same distance as, and in a same direction as, a portion of the transmission element that cooperates with the amplification means.

46. The dose indicator according to claim 21, wherein the transmission element is displaced in a translational direction.

47. The dose indicator according to claim 21, wherein a portion of the transmission element that cooperates with the moving part of the dispensing device is displaced a same distance as, and in a same direction as, a portion of the transmission element that cooperates with the amplification means.

48. The dose indicator according to claim 38, wherein the transmission element is displaced in a translational direction.

49. The dose indicator according to claim 38, wherein a portion of the transmission element that engages the dispensing device is displaced a same distance as, and in a same direction as, a portion of the transmission element that engages the spring.

50. The dose indicator according to claim 41, wherein the transmission element is displaced in a translational direction.

51. The dose indicator according to claim 42, wherein a portion of the transmission element that is attached to the cantilever spring is displaced the same distance as, and in a same direction as, a portion of the transmission element that engages the moving part of the dispensing device.

* * * * *